(12) United States Patent
Siegmund et al.

(10) Patent No.: US 10,195,001 B2
(45) Date of Patent: Feb. 5, 2019

(54) DENTAL IMPLANT MOUNTING SOLUTIONS WITH TRANSMUCOSAL COLLAR AND PATIENT-SPECIFIC MOUNTING HEADS ATTACHED DIRECTLY THERETO

(71) Applicant: 7075465 Manitoba Ltd., Winnipeg (CA)

(72) Inventors: Erik Siegmund, Winnipeg (CA); Lionel Gosselin, Winnipeg (CA)

(73) Assignee: Preferred Dental Implant Corp., Winnipeg, Manitoba ( * ) Notice: Subject to any disclaimer, the term of this patent is extended or adjusted under 35 U.S.C. 154(b) by 6 days.

(21) Appl. No.: 15/025,694

(22) PCT Filed: Sep. 26, 2014

(86) PCT No.: PCT/CA2014/050928
§ 371 (c)(1),
(2) Date: Mar. 29, 2016

(87) PCT Pub. No.: WO2015/042718
PCT Pub. Date: Apr. 2, 2015

(65) Prior Publication Data
US 2016/0235504 A1 Aug. 18, 2016

Related U.S. Application Data

(60) Provisional application No. 61/884,229, filed on Sep. 30, 2013.

(51) Int. Cl.
*A61C 8/00* (2006.01)
*A61C 13/00* (2006.01)

(52) U.S. Cl.
CPC ............ *A61C 8/0078* (2013.01); *A61C 8/006* (2013.01); *A61C 8/0063* (2013.01);
(Continued)

(58) Field of Classification Search
CPC ............................... A61C 8/0037; A61C 8/008
See application file for complete search history.

(56) References Cited

U.S. PATENT DOCUMENTS 4,634,561 A * 1/1987 DeLuca ................. A61C 13/20
156/89.11
5,116,225 A * 5/1992 Riera ..................... A61C 8/005
433/173
(Continued)

FOREIGN PATENT DOCUMENTS

| WO | 0004842 | 2/2000 |
| WO | 2012055039 | 5/2012 |
| WO | 2013059939 | 5/2013 |

*Primary Examiner* — Monica A Huson
*Assistant Examiner* — Kelsey C Grace
(74) *Attorney, Agent, or Firm* — Kyle R Satterthwaite; Ryan W Dupuis; Ade & Company Inc.

(57) ABSTRACT

A dental abutment or mounting head features a base of predetermined size and shape arranged for seating atop a flanged portion of a transmucosal collar that is fastened to a dental implant. An axial hole opens into the abutment/head from the underside thereof at a location arranged to align over an axial bore of the collar through which the collar is fastened to the implant. An upper portion of the abutment/head for supporting a dental prosthetic or framework is customized for the patient concerned. The predetermined base portion occupies substantially the entire face of the collar flange to provide optimal support of the abutment/head. As an interface between the implant and the abutment, the collar avoids the need to customize the base of the abutment to fit the particular brand or model of implant used, thereby reducing the amount of custom design and/or fabrication needed to fit the application.

9 Claims, 2 Drawing Sheets

(52) U.S. Cl.
CPC .......... *A61C 8/0068* (2013.01); *A61C 8/0074* (2013.01); *A61C 8/0077* (2013.01); *A61C 8/0089* (2013.01); *A61C 13/0004* (2013.01); *A61C 13/0019* (2013.01); *A61C 13/0022* (2013.01); *A61C 8/0069* (2013.01)

(56) References Cited

U.S. PATENT DOCUMENTS

| | | | |
|---|---|---|---|
| 5,362,235 A * | 11/1994 | Daftary | A61C 8/0048 433/172 |
| 5,571,015 A * | 11/1996 | Siegmund | A61C 8/005 433/173 |
| 5,662,473 A | 9/1997 | Rassoli et al. | |
| 2002/0125592 A1* | 9/2002 | Schulman | A61C 13/0003 264/16 |
| 2009/0325125 A1 | 12/2009 | Diangelo | |

* cited by examiner

DENTAL IMPLANT MOUNTING SOLUTIONS WITH TRANSMUCOSAL COLLAR AND PATIENT-SPECIFIC MOUNTING HEADS ATTACHED DIRECTLY THERETO

This application is the national stage of PCT/CA2014/050928, filed Sep. 26, 2014, and claims benefit under 35 U.S.C. 119(e) of U.S. Provisional Application Ser. No. 61/884,229 filed Sep. 30, 2013.

FIELD OF THE INVENTION

The present invention relates to dental implant solutions that employ a transmucosal collar as an intermediary between the dental implant body and an abutment for supporting a dental prosthetic, and more particularly to such a system in a which the abutment is customized according to the particular patient needs and mounted directly to the transmucosal collar.

BACKGROUND OF THE INVENTION

Applicant of the present invention previously proposed a unique dental implant mounting solution in PCT application publication WO 2013/059939, which built upon an earlier iteration of the system that was disclosed in U.S. Pat. No. 5,571,015.

The original U.S. patent introduced the use of a transmucosal collar screwed in place on a dental implant in order to seat a flanged intermediate portion of the collar atop the implant, and a also employed threaded cap engaged over a top end of the collar to enclose the axial bore of the collar in which the screw fixes the collar to the implant body. An angled configuration of top end of the cap and/or a top surface of the flanged portion of the collar was used to angularly offset an abutment that is attached to the top end of the cap from the longitudinal axis of the implant body, thus allowing the dental professional to achieve a suitable angle of the abutment for proper placement of the crown or other prosthetic regardless of the installed angle of the implant.

The subsequent PCT application built upon the original idea by providing the cap or mounting head with a contoured surface cooperable with a contoured-bottom abutment, whereby the abutment could be tilted relative to the mounting head and underlying collar and implant body in any direction to give even more freedom of angulation. The PCT application also revealed possible use of the collar to act as an adapter for providing attachment capability between attachments and implants that aren't directly compatible with one another, and also possible production of the collar in different axial lengths to allow selection from among these lengths to tailor the distance between the implant and abutment according to particular patient needs.

The presently disclosed invention further builds upon the transmucosal collar systems of the forgoing references.

SUMMARY OF THE INVENTION

According to one aspect of the invention there is provided a dental implant mounting system for supporting a dental prosthetic on a dental implant, the system the comprising:
 a transmucosal collar comprising a lower portion configured to coaxially engage an upper end of the dental implant, a flanged portion projecting radially outward relative to the lower portion at an upper end thereof, an axial bore passing fully through the transmucosal collar to open into the central implant at a lower end of the lower portion, the flanged portion having an annular upper face closing around the axial bore and facing away from the lower portion; and
 a dental abutment comprising a base portion portion having an underside arranged for seating atop the upper face of the flanged portion of the transmucosal collar, an axial hole opening into the dental abutment from the underside thereof at a location arranged to align over the axial bore of the transmucosal collar when seated on the upper face of the flanged portion thereof, and an upper portion extending from seating portion to form a support for mounting of a dental prosthetic, or a framework for supporting said dental prosthetic, to said upper portion of the dental abutment.

The transmucosal collar may comprise an externally threaded cylindrical upper portion upstanding from the flanged portion around the axial bore, in which case the system preferably further comprises an internally threaded cap arranged for threaded engagement onto the externally threaded cylindrical upper portion to close off an upper end of the axial bore at a top end of the cylindrical upper portion after threaded engagement of a fixation screw into the dental implant through the axial bore, wherein the axial hole of the dental abutment is a blind hole sized to accommodate receipt of the internally threaded cap, and the cylindrical upper portion of the transmucosal collar to which said cap is engaged, within the blind hole under seating of the abutment atop the flanged portion of the transmucosal collar.

In one embodiment, the abutment comprises castable material and the cap comprises cast-to material.

The cap may comprise a drive feature at a closed upper end of the cap for engagement by a rotational tool to drive threaded engagement of the cap onto the cylindrical upper portion of the transmuscosal collar.

As an alternative to a blind hole for covering a threaded cap of the collar, the axial hole of the abutment may comprise a through-hole passing fully through the abutment to accommodate threading of a fixation screw into the dental implant via the axial hole of the abutment and the axial bore of an uncapped transmucosal collar.

In such an embodiment, the abutment may comprise a lower portion that depends downward from the underside of the base portion around the axial hole while leaving an exposed area of the underside of the base portion for seating atop the upper face of the flanged portion of the transmucosal collar, wherein the flanged portion of the transmucosal collar features a recessed area of the upper face that is recessed around the axial bore relative to a surrounding region of the upper face and is sized to receive the lower portion of the abutment in said recessed area.

In such an embodiment, used in combination with the fixation screw, there may be provided a beveled shoulder within the axial hole of the abutment for engagement of a head of the fixation screw against said beveled shoulder under tightening of the fixation screw via the through-hole of the abutment.

The abutment may be made of a non-castable material, for example a zirconia selected from among of the varieties of zirconia in known use in the dental industry.

The abutment may have a footprint sized and shaped to fully overlie an entire surface area of the flanged portion of the transmucosal collar.

According to a second aspect of the invention there is provided a method of preparing a dental implant mounting system for mounting of a dental prosthetic to a dental implant, the method comprising the step of:

preparing a customized mounting head according to dental prosthetic placement and orientation requirements of a particular patient, including providing a customized shape to an upper portion of said mounting head that, in the finalized mounting head, resides overtop of a base portion of predetermined standardized configuration suited to support the customized mounting head atop a transmucosal collar of the implant mounting system that features a lower portion configured to coaxially engage an upper end of the dental implant, a flanged portion projecting radially outward relative to the lower portion at an upper end thereof, and an axial bore passing fully through the transmucosal collar to open into the central implant at a lower end of the lower portion.

The step of preparing the customized mounting head may comprise fabricating the upper portion customized using an additive manufacturing process, and may comprise fabricating an entirely of the mounting head using an additive manufacturing process.

The additive manufacturing process may be 3D printing.

The method may include fabricating at least part of the customized mounting head from castable material.

In on embodiment, the predetermined standardized configuration of the base portion of the mounting head comprises a blind hole of predetermined size opening into the base portion of the mounting head from an underside thereof to accommodate receipt of a cap that is threaded onto an externally threaded cylindrical upper portion of the transmucosal collar that is upstanding from the flanged portion of the transmucosal collar around the axial bore therein.

In another embodiment, the predetermined standardized configuration of the base portion of the finalized mounting head comprises a lower end portion of a through-hole passing fully through the mounting head to accommodate passage of a fixation screw through said through-hole of the mounting head, and onward through the axial bore of the transmucosal collar into the dental implant.

BRIEF DESCRIPTION OF THE DRAWINGS

In the accompanying drawings, which illustrate one or more exemplary embodiments of the present invention.

DETAILED DESCRIPTION

Figure 2:
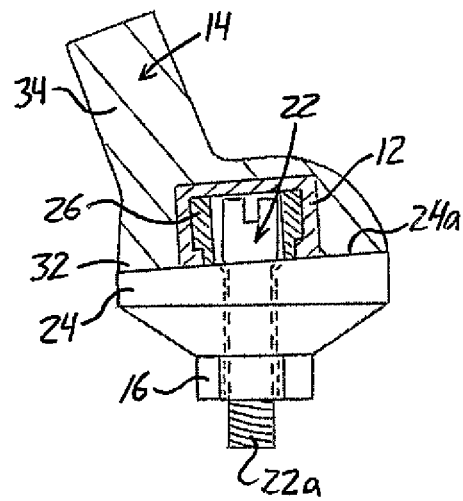
FIG. 2 is a partially cross-sectioned side elevational view of the first embodiment dental implant mounting system in an assembled state, featuring a patient-specific mounting head with an integrally defined abutment that has been customized according to the patient's requirements.
Figure 3:
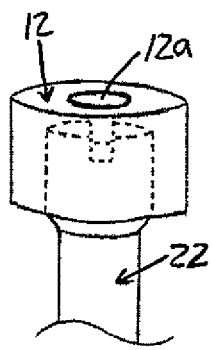
FIG. 3 is a cross-sectional view of a fixation screw and anti-rotational cap of the first embodiment dental implant mounting system of FIG. 2.
Figure 4:
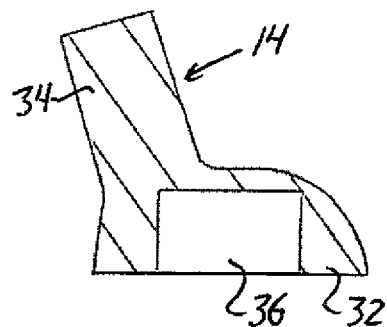
FIG. 4 is an isolated cross-sectional view of the patient specific mounting head of FIG. 2.

With reference to FIG. 2, a dental implant mounting system in accordance with the present invention includes a transmucosal collar 10 which is fastened to a dental implant (not shown) that is embedded into the jaw bone of a patient, an optional anti-rotational cap 12 to prevent loosening of a fixation screw that attached the collar to the implant, and a mounting head or base 14 which may be custom designed and manufactured with the use of computer assisted design (CAD) and subsequent 3D printing, CAD/CAM milling or similar methods of automated manufacture. This mounting base 14 may include a custom-defined angled abutment or similar integral structure for the support of an artificial tooth or dental restoration with the possibility of selected angular orientation varying from the longitudinal direction of the implant.

Figure 1:
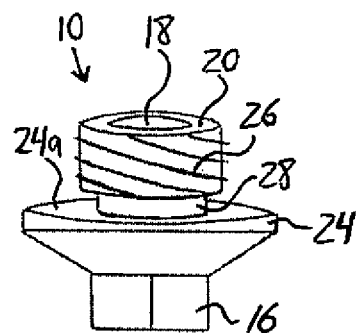
FIG. 1 is a side elevational view of a transmucosal collar of the type disclosed in Applicant's aforementioned PCT application, and used in a first embodiment dental implant mounting system of the present invention.

The transmucosal collar 10 of the embodiments of FIGS. 1 to 4, as shown in isolation in FIG. 1, is of the same general form as described in the aforementioned U.S. patent and PCT application, the entireties of which are incorporated herein by reference. The collar is thus comprised of a lower portion 16 configured to co-axially engage with the upper end of a dental implant. This portion may be designed to be compatible with any variety of connection methods utilized by dental implants (such as: internal hex, external hex etc.). The illustrated collar 10 is configured for cooperation with an internal-hex type implant that features a hexagonal recess at the upper end of the implant body that is coaxial with the longitudinal axial bore of the implant. The lower portion 16 of the collar thus features a hexagonally faceted outer periphery that fits concentrically within the hexagonally faceted recess of the implant's upper end in order to block radial sliding of the collar from the implant, and to prevent relative rotation between them around the axis of the implant.

An axial bore 18 passes fully through the transmucosal member from an upper end 20 of the upper portion 26 to a lower end of the lower portion 16 to allow passage of an externally threaded shaft 22a of a fixation bolt or screw 22 into the implant via the axial bore of the transmucosal collar in order to secure the transmucosal collar to the implant at a position situating an upper end of the fixation screw adjacent the upper end 20 of the upper portion of the transmucosal collar. The axial bore 18 of the transmucosal collar may include internal threading to allow for pre-guiding of the fixation screw 22 into the implant body and to help the dental professional when attaching the collar in awkward positions within the patient's mouth. As disclosed in the aforementioned PCT application, the interior bore may also contain a beveled shoulder to allow better force distribution along the fixation screw 22.

As also disclosed in the aforementioned U.S. patent and PCT application, the transmucosal collar may be manufactured with variations on the middle flange 24 that is located between lower and upper portions. Variations may include, thickness of the flange to allow for thicker gums (gingiva) in a patient, as well as angulations allowing for better aesthetics and emergence profile of the restoration. The flange may also act to secure single tooth restorations by engaging the artificial tooth, thereby preventing its rotation. In other words, when a single crown is placed on an abutment, there is a chance that the mounting base it is attached to may rotate. If the dental profession designs the crown or the coping of the crown so that it fits the flange, it may be performed in a way that prevents rotation. As an example: by shaping the flange on the transmucosal collar to an irregular shape by altering a portion of the flange's edge, with the crown or coping matching it and designed to fit around that non-circular shape, it cannot rotate. As another option, placing notches or other irregularities on the flange that the crown or coping will engage with may be used to prevent crown rotation.

In a first configuration of the mounting system of the present invention, shown in FIGS. 1 to 4, the transmucosal collar features an upper portion 26 which is externally threaded over a substantial majority of its axial span from its upper end 20 down toward the intermediate flange portion 24 of the collar. A reduced diameter cylindrical neck 28 joins the threaded area of the upper portion to the topside of the flanged portion 24 around the axial through bore of the collar.

In this first configuration of the mounting system, the threading of the upper portion 26 of the collar is designed to mate with an anti-rotational cap 12 that is comprised of a cylindrical or similarly shaped piece having a threaded blind-hole extending thereinto from a bottom end thereof. Ideally, this threading is reverse to that which is utilized by the fixation screw, thereby providing anti-rotational function (typically left vs. right hand threading) that prevents the fixation screw from backing out of its fully engaged position in the dental implant and collar. The outer surface of the anti-rotational cap 12 may be treated with grooves or surface roughening techniques to improve its bonding to the mounting head 12 when attached. When the fixation screw 22 is fully engaged to the transmucosal collar 10 (and trimmed as required if the head of the screw extends above the top end of the collar's bore when fully threaded into the implant) and the anti-rotational cap is attached, the preferred reverse threading makes rotation of the screw difficult. In addition, the ceiling of the blind-hole in the cap may rest on top of the screw that is partially received within the axial shaft of the transmucosal collar, thus holding the fixation screw in place.

Overtop of the anti-rotational cap 12 is placed the mounting head or base 14. This is composed of a lower seating or base portion 32 with a blind-hole extending thereinto from the bottom end 32 and an abutment portion 34 extending from the base portion at any of a number of varying angles or dimensions for the support of an artificial tooth or other dental restoration. The top of the anti-rotational cap 12 may have a slot or hexagonal recess 12a in its top surface designed to engage a dental implant driver to aid in tightening of the cap 12 prior to installation of the mounting head 14 thereover.

Utilizing CAD design software or similar, and ideally systems designed specifically for digital dentistry, the angle and dimensions of the extending abutment portion 34 of the mounting head 14 may be defined as required by the specific case. The resulting mounting base 14 may either then be milled utilizing CAD/CAM/CNC mills, or produced by additive manufacturing techniques, for example by 3D printers. In the case of 3D printing, the printed mounting base may be first printed in a castable wax or plastic and then cast in the desired dental material, or printed in the final material if the specifications of the specific printer permit.

This custom mounting base may be attached to the anti-rotational cap through a variety of methods including dental cements and adhesives, soldering or direct casting onto the cap. Attached in this way, the custom mounting base retains both anti-screw-loosening functionally and easy removability of the system via the reverse-threaded anti-rotational cap to which it is attached.

The embodiment of FIGS. 1 to 4, by employing a customized mounting head 14 that is produced to define a seamlessy integral abutment 34 according to the particular angulation and position requirements of the patient concerned can potentially provide such advantages as improved angulation and length accuracy over manually angled and trimmed abutments, and eliminating the need for a separate intermediary piece between the capped-off collar and the abutment.

Further advantages may be realized from the illustrated embodiments. For example, the first embodiment mounting head 14 in FIGS. 2 and 4 features a footprint that substantially covers the entire collar 12. The underside of the base portion 32 features a blind hole 36 extending centrally into the mounting head 14 in concentric alignment with the axial through bore of the mounting collar, but leaves an flat annular surface intact around the blind hole. The diameter of the blind hole only slightly exceeds the outer diameter of the cap 12, whereby this flat annular underside of the mounting head seated atop the flanged portion of the collar substantially covers the full available surface area of the top face 24a of the collar flange. Accordingly, the mounting head is maximizing the use of the available surface area on the collar in order to optimize the support provided to the abutment 34 that is monolithically incorporated as a seamlessly integral component of the single unitary body that defines the overall mounting head.

Figure 5:
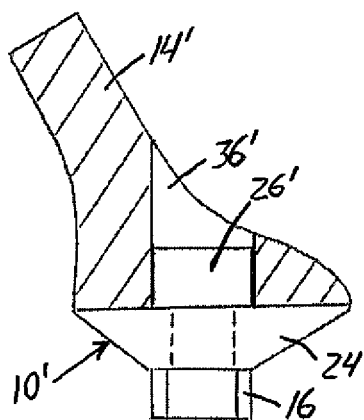
FIG. 5 is a partially cross-sectioned side elevational view of the transmucosal collar and patient-specific mounting head of a dental implant mounting system according to a second embodiment of the present invention.
Figure 6:
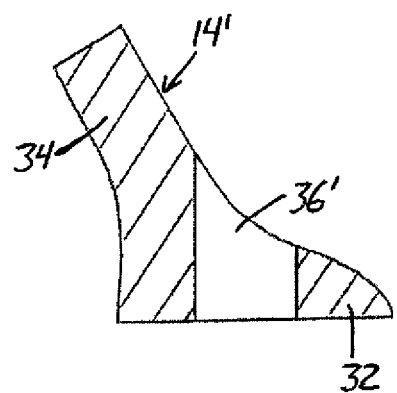
FIG. 6 is a cross-sectional view of the patient-specific mounting head of FIG. 5 in isolation.

In the second configuration of the transmucosal collar 10' shown in FIG. 5, the lower portion and middle flange remain identical, however the upper portion 26' is not threaded. It may be cylindrical in shape, or of a flat-sided or irregular shape in order to prevent rotation of the mounting base 14' around the longitudinal axis of the collar bore, and to provide better position-maintaining attachment. In this second configuration, the mounting base 14' may include an axial through-bore 36' rather than the blind-hole 36 of the first embodiment, in order to allow passage of, and access to, the fixation screw in the mounting collar via this throughbore 36'. This axial bore 36' may also include internal bevels or shoulders to allow the head of a fixation screw of extended length to rest at this shouldered or beveled point of the mounting head rather than within the transmucosal collar. Although this embodiment lacks the rotation-prevention for the fixation screw due to the lack of a cap, it shares the same benefits of the first embodiment in regards to a single-piece mounting head and abutment combination and direct seating and mounting of the abutment on the topside of the collar flange.

Figure 7:
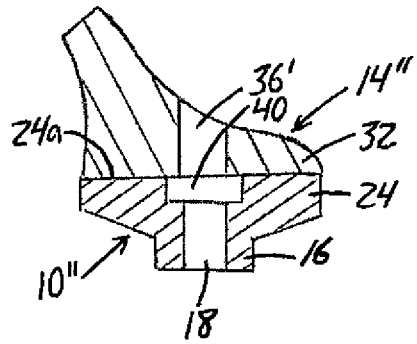
FIG. 7 is a partially cross-sectioned side elevational view of the transmucosal collar and patient-specific mounting head of a dental implant mounting system according to a third embodiment of the present invention.
Figure 8:
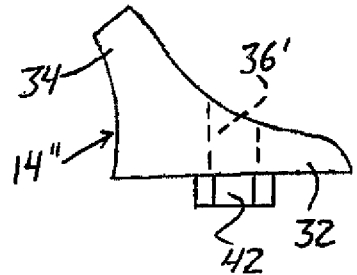
FIG. 8 is a cross-sectional view of the patient-specific mounting head of FIG. 7 in isolation.

In a final configuration of the mounting system shown in FIGS. 7 and 8, the topside of the flanged intermediate portion 24' of the transmucosal collar 10" possesses an internal recess 40 that is wider in diameter than the axial bore 18 for the fixation screw and shallower than the axial bore in terms of axial depth along the collar's longitudinal axis. This recess 40' is designed to mate with a projecting bottom portion 42 of the mounting base 14, thereby connecting the two pieces. This bottom portion 42 of the mounting base 14 depends axially downward therefrom in a concentric position around the axial through-hole 36' thereof, but has a radial reach less than the overlying base portion 32 of the mounting base 14, whereby the underside of the base portion 32 still has an exposed annular bottom surface closing around the projecting bottom portion 42 and the axial bore 36' to enable seating of this annular surface on the top face 24a of the collar flange 24.

As demonstrated by the illustrated embodiments, notable angulation can be achieved by angular offsetting of an elongated abutment portion 34 of the mounting head 14 that juts obliquely upward from a base portion that closes annularly around the collar bore 18 on the top surface of the collar flange 24. In the case of the first embodiment, the base portion 32 not only circumferentially surrounds the collar bore and any cap 12 isntalled thereover, but also fully closes overtop of the collar bore and cap 12. As shown, use of a collar of non-uniform flange thickness can also be used to attain an obliquely tilted orientation of the flange's top surface 24a relative to the collar bore 18 in order to likewise tilt the flat annular bottom of the mounting head 14 in the same direction as the inclination angle of the abutment portion 34, thereby further increasing the angulation of the abutment relative to the longitudinal axis of the dental implant body.

Oral scanning equipment and dental design software may be used to scan a digital map of a patient's and generate a virtual dental model for computer aided design of a mounting head with the abutment portion fully customized according to the angulation and positional requirements of the particular patient's model. In the case of 3D printing, the software provided to a dental lab for such purposes may be pre-loaded with base-portion specifications for printing the lower portion of the mounting head with suitable base features for mating with one or more predefined types or models of transmucosal collars, whereby the standardized base features and patient-specific customized abutment feature can be amalgamated by the software for automated fabrication of the overall single-piece mounting head that can therefore be directly attached to a capped or uncapped collar without further intermediary pieces.

In the case of CNC milling or any other possible subtractive types of automated manufacturing, the software may likewise be configured to combine the geometric data of the patient-specific customized portion of the mounting head with predefined base feature data so as to machine all these features, or the lab may be provided with milling blocks that have already been factory-equipped with collar-compatible mounting features at the end of the block that defines the base portion for seating on the collar flange, in which case the laboratory equipment need only machine out the patient-specific customized upper portion of the mounting head.

Although the customized portion of the illustrated mounting head features a generally cylindrical or externally tube-like abutment shape in order to generally reflect a conventional generally implant abutment shape for supporting a crown, the head/abutment may be printed with alterations to such shape/dimension in order to more accurately fit a framework/coping/crown of any of a variety of different types, which may also be designed via digital dental software. As 3D printing is expanding into printing frameworks, coping etc. (the structures that fit 'on top' of the abutment) the potential to design both the copings and the abutment simultaneously in preparing a case from digital files allow the user to print an abutment that is precisely designed to fit the coping/framework/crown. The system of the present invention basically acts as the interface between the implant root (in the jaw) and the coping/crown/etc. 'on top', and the ability to completely customize or alter the mounting head shape based on the design requirements of the restoration may be an important feature. At the same time, the transmucosal collar acts as an interface between the implant and the mounting head, and avoids the need to customize the base of the abutment to fit the particular brand or model of implant used, thereby reducing the amount of custom design and/or fabrication needed to fit the application.

Since various modifications can be made in my invention as herein above described, and many apparently widely different embodiments of same made within the spirit and scope of the claims without department from such spirit and scope, it is intended that all matter contained in the accompanying specification shall be interpreted as illustrative only and not in a limiting sense.

The invention claimed is:

1. A method of preparing a dental implant mounting system for mounting of a dental prosthetic to a dental implant, the method comprising the step of:
    obtaining a customized mounting head that has been custom fabricated according to dental prosthetic placement and orientation requirements of a particular patient, and that possesses a customized shape at an upper portion of said mounting head that resides overtop of a base portion of predetermined standardized configuration having a blind hole that extends into the base from an underside thereof and terminates at a closed upper end at which said blind hole is fully covered by the upper portion of the mounting head;
    obtaining a transmucosal collar that features a lower portion configured to coaxially engage an upper end of the dental implant, a flanged portion projecting radially outward relative to the lower portion at an upper end thereof, an externally threaded upper portion upstanding from the flanged portion, and an axial bore passing fully through the transmucosal collar from a top end of the externally threaded upper portion to a lower end of the lower portion;
    obtaining an internally threaded cap having a threaded blind hole extending thereinto from a bottom end thereof and terminating at a closed top end of said threaded blind hole at which at which said threaded blind hole is fully covered by a top wall of said cap;
    threading a fixation screw into the implant through the axial bore of the transmucosal collar, thereby fastening the transmucosal collar to the implant;
    installing the internally threaded cap and the customized mounting head on the transmucosal collar, during which the internally threaded cap is placed in a position in which (i) the internally threaded cap is threaded onto the externally threaded upper portion of the transmucosal collar, (ii) the internally threaded cap is located inside the blind hole of the customized mounting head, and (iii) the closed top end of the threaded blind hole in the internally threaded cap and the closed upper end of the blind hole in the mounting head both overlie the axial bore of the transmucosal collar and thereby fully enclose the fixation screw therein; and
    attaching the customized mounting head to the internally threaded cap.

2. The method of claim 1 wherein the step of obtaining the customized mounting head comprises fabricating the upper portion customized using an additive manufacturing process.

3. The method of claim 1 wherein the step of obtaining the customized mounting head comprises fabricating an entirely of the mounting head using an additive manufacturing process.

4. The method of claim 2 wherein the additive manufacturing process is 3D printing.

5. The method of claim 1 comprising fabricating at least part of the customized mounting head from castable material.

6. The method of claim 1 wherein the step of attaching the customized mounting head to the internally threaded cap comprises casting the customized mounting head to the internally threaded cap.

7. The method of claim 1 wherein the step of attaching the customized mounting head to the internally threaded cap comprises cementing the customized mounting head to the internally threaded cap.

8. The method of claim 1 wherein the step of attaching the customized mounting head to the internally threaded cap comprises soldering the customized mounting head to the internally threaded cap.

9. The method of claim 1 wherein the step of attaching the customized mounting head to the internally threaded cap comprises adhering the customized mounting head to the internally threaded cap.

* * * * *